United States Patent [19]
DiGregorio et al.

[11] Patent Number: 5,856,150
[45] Date of Patent: Jan. 5, 1999

[54] SELECTIVE HYDROLYSIS OF SATURATED ESTERS OVER UNSATURATED ESTERS USING ENZYMES

[75] Inventors: Kevin Andrew DiGregorio, Cross Lanes; James Charles Hatfield, St. Albans; George Ernest Keller, South Charleston, all of W. Va.

[73] Assignee: Amerchol Corporation, Edison, N.J.

[21] Appl. No.: 928,413

[22] Filed: Sep. 12, 1997

Related U.S. Application Data

[63] Continuation of Ser. No. 733,870, Oct. 18, 1996, abandoned.
[51] Int. Cl.[6] ............................... C12P 7/40; C12P 7/54; C12P 7/52
[52] U.S. Cl. ..................... 435/136; 435/140; 435/141; 435/262; 435/264; 523/102; 526/77
[58] Field of Search ................................ 435/136, 140, 435/141, 262, 264; 523/102; 526/77

[56] References Cited

U.S. PATENT DOCUMENTS

| | | |
|---|---|---|
| 4,003,865 | 1/1977 | Nowak et al. . |
| 4,017,364 | 4/1977 | van Leemputten . |
| 4,283,491 | 8/1981 | Dappen . |
| 4,897,352 | 1/1990 | Chonde et al. . |
| 5,145,890 | 9/1992 | Frederick . |
| 5,422,269 | 6/1995 | Nicks et al. . |

FOREIGN PATENT DOCUMENTS

| | | |
|---|---|---|
| 0101046A1 | 8/1983 | European Pat. Off. . |
| 0288203A2 | 4/1988 | European Pat. Off. . |
| 1201459 | 3/1969 | United Kingdom . |
| 2215335 | 3/1988 | United Kingdom . |

OTHER PUBLICATIONS

APS Abstract Japan 58–165796 Murase et al Sep. 30, 1983.

Waley, S.G., Mechanisms of Organic and Enzymic Reactions, Oxford University Press, London (1962), pp. 233–249.

Alvarez, F.J., Stella, V.J., Pharm. Res. 6(7), 555–63 (1989), "Pancreatic lipase–catalyzed hydrolysis of estersof hydroxymethyl phenytoin dissolved in various metabolizable vehicles, dispersed in micellar systems, and in aqueous suspensions."

Jones, J.B., Ann. N.Y. Acad. Sci. 501, 119–128 (1987), "Some examples of enzymes in organic synthesis."

Bell, G., Blain, J.A., Patterson, J.D.E., Shaw, C.E.L., Todd, R., FEMS Microbiology Letters 3, 223–225 (1978), "Ester and glyceride synthesis by *Rhizopus arrhizus* mycelia."

Oesterberg, E., Ristoff, C., Holmberg, K., Tenside, Surfactants, Deterg. 25(5), 293–7 (1988), "Lipase catalyzed hydrolysis."

Sanders, J.M., Burja, L.T., Matthews, H.B., Drug Metabolism and Disposition 16(3), 429–434 (1988), "Metabolism and disposition of n–butyl acrylate in male Fischer rats."

Salleh, A.B., Yunus, W.M., Abdul Rahman, R.N., Ibrahim, A., Proc. Malays. Biochem Soc. Conf., 12th, 26–9 (1986), "Poly(ethyl acrylate–divinylbenzene) as a matrix for coupling enzyme."

Bar–Eli, A., Katchalski, E., Nature 188(4753), 856–857 (Dec. 3, 1960), "A water–insoluble trypsin derivative and its use as a trypsin column."

Maxim, S., Flondor A., Revue Roumaine de Chimie 34(6), 1389–95 (1989), "New crosslinked functionalized acrylic copolymers for biotechnological applications."

Mattson, F.H, Volpenhein, R.A., J. Lipid Res. 10(3), 271–6 (1969), "Relative rates of hydrolysis by rat pancreatic lipase of esters of C2–18 fatty acids with C1–18 primary n–alcohols"–.

Quinn, D.M., Biochemistry 24(13), 3144–9 (1985), "Solvent isotope effects for lipoprotein lipase catalyzed hydrolysis of water–soluble p–nitrophenyl esters."

O'Connor, C.J., Mitha, A.S.GH., Aust. J. Chem. 39(2), 259–69 (1986), "Studies in bile salt solutions, XIV, Electronic, charge, and steric substrate–effects on the esterase activity of bile–salt–stimulated human milk lipase. Hydrolysis of 4–substituted phenyl propionates."

Wu, S.H., Guo, Z.W., Sih, C.J., J. Am. Chem. Soc. 112(5), 1990–5 (1990), "Enhancing the enantioselectivity of Candida lipase–catalyzed ester hydrolysis via noncovalent enzyme modification."

Cambou, B., Klibanov, A.M., J. Am. Chem. Soc. 106, 2687–2692 (1984), "Preparative production of optically active esters and alcohols using esterase–catalyzed sterospecific transesterification in organic media."

Cambou, B., Klibanov, A.M., Biotechnology and Bioengineering 26, 1449–1454 (1984), "Comparison of different strategies for the lipase–catalyzed preparative resolution of racemic acids and alcohols:asymmetric hydrolysis, esterification, and transesterification."

Cesti. P. Zaks, A. Klibanov, A.M., Applied Biochemistry and Biotechnology 11, 401–407 (1985), "Preparative regioselective acylation of glycols by enzymatic transesterification in organic solvents."

Dahl, A.R., Miller, S.C., Petridou–Fischer, J., Toxicology Letters 36, 129–136 (1987), "Carboxylesterases in the respiratory tracts of rabbits, rats and Syrian hamsters."

Klibanov, A.M., Samokhin, G.P., Martinek, K. Berezin, I.V., Biotechnology and Bioengineering 19, 1351–1361 (1977), "A new approach to preparative enzymatic synthesis."

Vidaluc, J.L., Baboulene, M. Speziale, V., Lattes, A. Tetrahedron 39(2), 269–274 (1983), "Optimization of the enzymatic synthesis of amino acid esters, reaction is polyphasic medium."

(List continued on next page.)

*Primary Examiner*—Herbert J. Lilling

[57] ABSTRACT

Processes are disclosed for the selective hydrolysis of saturated esters, e.g., ethyl propionate, over unsaturated esters, e.g., ethyl acrylate, using enzymes, e.g., lipases. The processes are useful, for example, for removing undesired esters from monomer feeds used in latex polymerization and from the latexes after polymerization. The processes can be used, for example, to treat latexes used in hair fixative compositions to remove unpleasant odors.

20 Claims, No Drawings

OTHER PUBLICATIONS

Heimermann, W.H. Holman, R.T. Gordon, D.T., Kowalyshyn, D.E., Jensen, R.G., Lipids 8(1), 45–7 (1973), "Effect of double bond position in octadecenoates upon hydrolysis by pancreatic lipase."

Tor, M. Chen. W., Bengtsson–Olivecrona, G., Aakesson, B., Nilson, A., Biochim. Biophys, Acta 1075(3), 259–66 (1991), "Hydrolysis of chylomicron polyenoic fatty acid esters with lipoprotein lipase and hepatic lipase."

Lie, E. Molin, G., J. Chem. Tech. Biotechnol. 50, 549–53 (1991), "Hydrolysis and esterification with immobilized lipase on hydrophobic and hydrophilic zeolites."

Corkill, J.A., Lloyd, E.J., Hoyle, P., Crout, D.H.G., Ling, R.S.M., James M.L., Piper R.J., Clin. Chim. Acta 68, 141–146 (1976), "Toxicology of methyl methacrylate: the rate of disappearance of methyl methacrylate in human blood in vitro."

Crout, D.H.G. Corkill, J.A. James, M.L. Ling, R.S.M, Clin. Orthop. Rel. Res. 141, 90–95 (1979), "The hydrolysis of methyl methacrylate to methacrylic acid during total hip replacement".

Miller, R.R., Ayres, J.A. Rampy, L.W. McKenna, M.J. Fundamental and Applied Toxicology 1, 410–14 (1981), "Metabolism of acrylate esters in rat tissue homogenates."

Klibanov, A.M., Siegel, E.H., Enzyme Microb. Technol. 4, 172–174 (1982), "Geometric specificity of porcine liver carboxylesterase and its application for the production of cis–arylacrylic esters."

Scott, W.T., McKenna, M.J., Fundamental and Applied Tosicology 5, 399–404 (1985), "Hydrolysis of several glycol ether acetates and acrylate esters by nasal mucosal carboxylesterase in vitro."

Ghanayem, B.I. Burka, L.T., Matthews, H.B., Fundamental and Applied Toxicology 9, 389–397 (1987), "Ethyl acrylate distribution, macromolecular binding, excretion, and metabolism in male Fisher 344 rats."

Silver, E.H., Murphy, S.D., Toxicol. Appl. Pharmacol. 57, 208–219 (1981), "Potentiation of acrylate ester toxicity by prior treatment with the carboxylesterase inhibitor triorthotolyl phosphate (TOTP)."

Vodicka, P. Gut, I. Frantik, E., Toxicology 65, 209–221 (1990), "Effects of inhaled acrylic acid derivatives in rats."

Tor, R., Dror, Y., Freeman, A., Enzyme Microb. Technol. 12, 299–304 (Apr., 1990), "Enzymatically catalyzed transesterification of acryl and methacryl monomeric esters."

McCarthy, T.J., and Witz, G., Adv. Exp. Med. Biol. 283, 333–335 (1991), "Structure–activity relationships of acrylate esters: Reactivity towards glutathione and hydrolysis by carboxylesterase in vitro."

Klibanov, A.M., Adv. Appl. Microb. 29, 1–28 (1983), "Stabilization of enzymes against thermal inactivation."

Tor, R., Dror, Freeman, A., Enzyme Microb. Technol. 11, 306–312 (1989), "Enzyme stabilization by bilayer encagement."

Weetall, H.H., Immobilized enzymes for industrial reactors (ed. R.A. Messing), Academic Press, New York (1975), chapter 6, pp. 99–123, "Immobilization by covalent attachment and by entrapment."

Kitano, H., Nakamura, K., Ise, N.J. of Applied Biochemistry 4, 487–95 (1982), "Functionalized polymer latices."

Bahadur, A., Bahadur, P., Indian J. of Biochemistry & Biophysics 22, 107–110 (Apr. 1985), "Trypsin immobilization on anionic polymeric latex."

SELECTIVE HYDROLYSIS OF SATURATED ESTERS OVER UNSATURATED ESTERS USING ENZYMES

This application is a Continuation of prior U.S. application Ser. No. 08/733,870, Filing Date Oct. 18, 1996, now abandoned.

FIELD OF THE INVENTION

The present invention generally relates to the use of enzymes to hydrolyze esters. More specifically, the present invention relates to methods for selectively hydrolyzing saturated esters, such as, for example, ethyl propionate, over unsaturated esters, such as, for example, ethyl acrylate, both of which are often present in latex compositions.

BACKGROUND OF THE INVENTION

Latex polymers can be made from a variety of ethylenically unsaturated monomers. Lower alkyl acrylates, e.g., those having from 1 to about 5 carbon atoms, are often employed as starting materials to make acrylic latexes. Most latexes, including acrylic latexes, contain residual monomers or impurities, some of which are benign and some of which can impart an unpleasant odor. Acrylic latexes made from ethyl acrylate often contain an analog, ethyl propionate, as an impurity with the ethyl acrylate monomer. Ethyl propionate can be a source of a residual odor which is undesirable in the latex product. Ethyl propionate levels must often be reduced to less than about 20 ppmw or lower to render the latex suitable for personal care use. In addition, residual unsaturated monomers, such as, for example, ethyl acrylate, are also often removed from latex polymers as these materials can be undesirable in the latex product.

It is not uncommon to treat latex polymers to remove residual monomers and impurities. For example, latexes can be treated with enzymes to hydrolyze such materials. Such treatments typically reduce the levels of the unsaturated esters as well as the saturated esters.

When treating the monomer starting material, it can be desirable to selectively remove the saturated analogs, e.g., ethyl propionate, from the unsaturated monomer, e.g., ethyl acrylate. Enzymes that do not selectively hydrolyze the saturated over the unsaturated species will unnecessarily degrade useful monomer.

When treating the latex instead of the monomer starting material to remove the saturated impurities, selective reaction of saturated over unsaturated esters is also desirable. In typical latex manufacture, for reasons related both to odor and toxicity, effort is made to reduce the residual level of unreacted monomer. One common measure to reduce the residual level of monomer is a period of post-heating of the latex after the polymerization is substantially complete during which the latex is held at an elevated temperature for a period of time to further react any residual monomer. Another common measure is the use of additional initiator to generate a fresh batch of free radicals during the post-heat period which react with residual monomer and so reduce its level. Such measures often have the effect of reducing the residual monomer level to values of 50 ppmw and less, often 20 ppmw and less. In contrast, the residual level of saturated ester species which is unreactive remains at higher levels, e.g., 80 to 140 ppmw or more depending on the level of saturated species in the original monomer feed and the relative amount of each monomer used in the monomer mix. Thus, the saturated concentration is typically greater than the unsaturated (or monomer) concentration in the final latex. An enzyme that selectively reacts with the species present in higher concentration is more efficient and economical than one that is not selective.

Therefore, processes are desired for selectively hydrolyzing saturated esters, e.g., ethyl propionate, over unsaturated esters, e.g., ethyl acrylate, using enzymes.

SUMMARY OF THE INVENTION

By this invention, processes are provided for the selective removal of saturated esters, e.g., ethyl propionate, over unsaturated esters, e.g., ethyl acrylate, by hydrolyzing the esters to the corresponding acid and alcohol with certain enzymes. The enzymes include those which are effective to selectively hydrolyze the saturated esters, e.g., lipase enzymes and esterase enzymes. By virtue of the present invention, it is now possible to conduct the hydrolysis on the monomer feeds prior to latex polymerization or after the polymerization of the monomers to form the latex.

Personal care products, e.g., hair sprays, made from monomers or latexes treated with the enzymes in accordance with the present invention often have a more pleasant odor than those which are not treated with such enzymes.

DETAILED DESCRIPTION OF THE INVENTION

In general, the esters which can be hydrolyzed in accordance with the present invention are not critical and can, for example, be short or long chain esters, e.g., from about 3 to about 20 carbon atoms per molecule. Preferably, the esters are saturated esters wherein the alkyl group has from 1 to about 5 carbon atoms per molecule, e.g., ethyl propionate.

Alkyl acrylate monomers such as, for example, ethyl acrylate, typically comprise from about 10 ppmw to 10 wt % of the saturated ester, e.g., ethyl propionate, and from about 70 to 99 wt % or more the unsaturated ester and less than about 10 wt % water. Often, the concentration of the saturated ester in the monomer feed is from about 10 to 800 ppmw. The concentration of the saturated ester in the latex is typically the same as in the monomer feed, diluted by other ingredients added during the polymerization. Typical concentrations of the saturated ester in the latex prior to enzyme treatment are from about 10 to 500 ppmw, often from about 50 to 250 ppmw based on the total weight of the latex (polymer plus water). The concentration of residual unsaturated esters, e.g., ethyl acrylate, prior to enzyme treatment is typically from about 10 to 500 ppmw and often from about 20 to 100 ppmw in the latex based on the total weight of the latex. The latex typically further comprises about 40 to 90 wt % water in addition to the polymer which comprises from about 10 to 60 wt % of the latex. Preferably, the concentration of the saturated ester in either the monomer feed or the latex product after treatment in accordance with the present invention is less than about 20 ppmw and more preferably from about 0 to 10 ppmw. The concentration of unsaturated ester in the latex product after enzyme treatment is typically from about 0 to 20 ppmw and preferably from about 0 to 10 ppmw based on the total weight of the latex.

The latexes suitable for treatment in accordance with the present invention are not critical and include, for example, polymers containing acrylic, vinyl and unsaturated acid monomers. Preferred polymers comprise a copolymer of (a) about 35 to 74 weight percent of an alkyl acrylate wherein the alkyl group contains from 1 to 5 carbon atoms; (b) about 25 to 65 weight percent of an alkyl methacrylate wherein the alkyl group contains from 1 to 5 carbon atoms; and (c) about 1 to 15 weight percent of one or more acrylate acids or salts thereof having from 3 to 5 carbon atoms. More than one monomer species from each of the above monomer groups can be employed in the preferred latexes of the present invention.

Preferred alkyl acrylate monomers include methyl acrylate, ethyl acrylate, propyl acrylate and butyl acrylate. Ethyl acrylate is especially preferred. The concentration of alkyl acrylate monomer is preferably from about 40 to 70 weight percent and, more preferably, from about 50 to 60 weight percent of the polymer composition, i.e., solids of the latex.

Preferred alkyl methacrylate monomers include methyl methacrylate, ethyl methacrylate, propyl methacrylate and butyl methacrylate. Methyl methacrylate is especially preferred. The concentration of alkyl methacrylate monomer is preferably from about 30 to 50 weight percent and, more preferably, from about 30 to 40 weight percent of the polymer composition.

Preferred acrylate acids include acrylic acid, methacrylic acid, crotonic acid, itaconic acid and mixtures thereof. Acrylic acid and methacrylic acid are especially preferred. The concentration of acrylate acids is preferably from about 5 to 15 weight percent and, more preferably, from about 8 to 12 percent of the polymer composition. In one especially preferred aspect of the invention, both acrylic acid and methacrylic acid are employed, each in a concentration range of from about 2 to 10 weight percent, with the total not exceeding about 15 weight percent.

The preferred latexes suitable for treatment in accordance with the present invention are typically in colloidal form, i.e., aqueous dispersions, and can be prepared by emulsion polymerization in the presence of a chain transfer agent and an initiator. Specific details concerning procedures and conditions for emulsion polymerization are known to those skilled in the art. Typically, however, the polymerization is carried out in an aqueous medium at a temperature of from about 35° to 90° C. The pressure is not critical and is dependent upon the nature of the monomers employed. Preferably, the copolymer is substantially non-crosslinked, i.e., less than about 1 percent crosslinked.

In accordance with the present invention, it has been found that the presence of certain types of surfactants in the final polymer composition can enhance the freeze-thaw stability of the polymer composition. Preferably, the surfactant is effective to inhibit flocculation and viscosity increases due to subjection to freeze-thaw cycles. Quite surprisingly in accordance with the present invention, it has been found that surfactants with a surface tension of greater than 32.2 dynes/cm and less than 48.2 dynes/cm can provide enhanced freeze-thaw stability. Preferably, the surface tension of the surfactant will be from about 35 to 45 dynes/cm. As used herein, the surface tension of the surfactant is the surface tension measured at a surfactant concentration of 0.10 weight percent in water. Techniques for measuring surface tension are known to those skilled in the art. Preferably, the surfactant is a nonionic, alkoxylated surfactant. The surfactant may also contain anionic groups such as, for example, sulfates. Often, the surfactant will contain both nonionic and anionic portions, such as, for example, in the case where the surfactant is sulfated. Preferably, the surfactant is selected from the group consisting of alkoxylated phenols, alkoxylated alcohols and mixtures thereof. It is further preferred that the surfactant contains an alkyl portion having from about 6 to 18 carbon atoms per molecule and, more preferably, from about 8 to 15 carbon atoms per molecule.

Preferably, the alkoxylated surfactant is ethoxylated and contains from about 2 to 50 and, more preferably, from about 9 to 40 moles of ethylene oxide substitution per molecule. One particularly preferred class of surfactants for use in accordance with the present invention are ethoxylated linear secondary alcohols, such as, for example, Tergitol 15S40 sold by Union Carbide Corporation, Danbury, Conn. Other particularly preferred classes of surfactants suitable for use in accordance with the present invention are nonyl phenol ether sulfates, such as, for example, Aerosol NPES 930 and Aerosol NPES 2030, sold by Cytec Industries, Inc., West Paterson, N.J. and monoester sulfosuccinates such as, for example, Aerosol A 102 sold by Cytec Industries, Inc.

The surfactant, or mixtures of surfactants, added for enhancing freeze-thaw stability can either be introduced prior to or during the polymerization reaction or, alternatively, added to the polymer composition upon completion of the polymerization. Moreover, the surfactants used for freeze-thaw stability can be the same or different from the surfactants used for the polymerization. Preferably the total concentration of surfactants in the polymer composition is from about 0.01 to 1.0 weight percent, more preferably from about 0.05 to 0.5 weight percent, most preferably, from about 0.1 to 0.3 weight percent.

The molecular weight of the surfactant suitable for use in accordance with the present invention can vary widely and can typically range from about 500 to 2000 grams per gram mole or more.

In accordance with the present invention, in addition to providing a surfactant in the polymer composition, the particle size of the copolymer is preferably controlled in order to enhance freeze-thaw stability. It has been found that at particle size levels of less than about 0.1 micron, the freeze-thaw stability of latexes is inferior to that of particles larger than 0.1 micron. Latexes having particle sizes greater than about 1 micron may have acceptable freeze-thaw stability, but such larger particles can settle which is generally undesirable. Typically, at least 95 weight percent of the copolymer will have an average particle size from about 0.1 to 1 micron, preferably from about 0.1 to 0.5 micron.

In addition to the use of the processes of the present invention, in order to control the level of residual monomers remaining in the polymer composition, it is preferred to add an initiator a second time after the polymerization has substantially completed, e.g., greater than about 90 percent conversion. In this manner, it is possible to maintain the level of residual alkyl acrylate below about 100 ppmw, preferably below about 50 ppmw, and, most preferably, below about 20 ppmw. In addition, it is preferred that the residual level of the other monomers in the composition is less than about 50 ppmw and preferably less than about 20 ppmw for each.

Often, the concentration of copolymer, i.e., solids content, in the polymer composition can be as high as about 50 weight percent, occasionally as high as about 60 weight percent or higher. Preferably, the concentration of copolymer is from about 10 to 60 weight percent and, more preferably, from about 20 to 50 weight percent of the polymer composition.

The pH of the polymer composition typically ranges from about 2 to 8. When the pH is at the low end of the range, it can be increased by introducing a suitable base such as ammonia, alkali metal hydroxides or organic amines. One preferred pH range for the polymer composition is from about 3 to 6 since a lower pH generally provides greater resistance to bacteria, smaller particle size and lower viscosity than a higher pH. Another preferred pH range for the polymer composition is from about 6 to 8, since it is more compatible with skin and hair than the lower pH range.

The viscosity of the polymer composition will typically be from about 5 to 15 centipoise ("cP") at 25° C. The surface tension of the polymer composition will typically be from about 10 to 50 dynes/cm at 25° C. It is believed that the low viscosity and surface tension of the polymer compositions contribute to their desirable properties when used in hair spray compositions.

The polymer compositions of the present invention are particularly useful in hair care compositions, such as, for example, hair lotions, hair creams, hair gels and mousses, and hair spray compositions. Further details of such hair care compositions are known to those skilled in the art, see, e.g., U.S. Pat. No. 5,413,775.

The enzymes suitable for use in accordance with the present invention are those which are effective to hydrolyze esters. Preferably, the enzymes have selectivity for saturated esters, e.g., ethyl propionate, over unsaturated esters, e.g., ethyl acrylate. Lipases and esterases are especially preferred. The enzymes suitable for use in accordance with the present invention can be immobilized, i.e., loaded on a support such as, for example, an acrylic support, or used in their unsupported, i.e., neat, form. Preferred lipases include *Candida rugosa*, Wheat Germ, Porcine Pancreas, *Rhizopus arrhizus, Candida antarctica, Mucor miehei*, Fungal origin, Pseudomonas species, *Candida lipolytica, Humicola langinosa* and Mucor javanicus. *Candida antarctica* lipase enzymes are especially preferred. Such enzymes are commercially available. Further details of such enzymes are known in the art. See, for example, U.S. Pat. No. 5,145,890, issued Sep. 8, 1992.

The enzymes can be used to hydrolyze the saturated ester, either by pretreating the monomer feed or posttreating the latex. Pretreatment preferably utilizes enzyme catalyzed hydrolysis in an organic phase while posttreatment is preferably carried out in an aqueous phase (the latex particles are suspended in water). The chemistry, showing the desired selective hydrolysis of ethyl propionate in bulk ethyl acrylate, is given below. The resulting propionic acid and ethanol are benign.

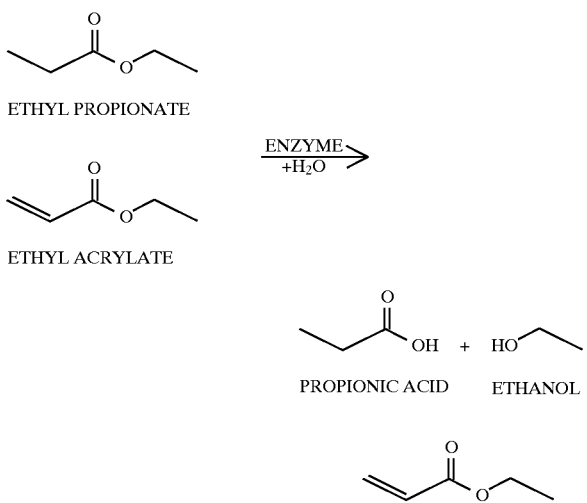

The processes of the present invention can be carried out by a continuous or batch process. In batch processes, the enzyme is added to either the monomer feed or the latex, and the hydrolysis is conducted to remove the saturated ester, and if desired the unsaturated ester. As used herein, the term "feed" is used with reference to: (i) the monomer feed containing both the unsaturated ester and the saturated ester in the organic phase; or (ii) the latex which contains the latex polymer, saturated ester and any residual unsaturated ester. Preferably, the enzyme is added to the feed at a concentration of from about 0.1 ppmw to 10 wt % (100,000 ppmw), preferably from about 0.1 to 100 ppmw and more preferably from about 0.1 to 10 ppmw based on the total weight of the feed. The pH of the feed is typically from about 4 to 8, preferably from about 5 to 7. The temperature at which the enzyme treatment is conducted is typically from about 0° to 80° C., preferably from about 20° to 50° C. and more preferably from about 25° to 40° C. and most preferably from about 30° to 40° C. The pressure used is not critical and typically ranges from about 0.8 to 1.2 atmospheres absolute. The enzyme reaction time is typically from about 0.5 to 24 hours, preferably from about 1 to 16 hours.

In a preferred aspect of the invention, the enzyme is introduced into the latex product just prior to drumming the product and the hydrolysis substantially takes place during transportation and storage. Thus, the enzyme is added to the feed and the feed is separated into a plurality of portions prior to any significant hydrolysis, i.e., less than 5% conversion, of the saturated ester. Preferably, each portion of the latex is introduced into a separate container, e.g., drum, before such hydrolysis takes place. Quite advantageously, the agitation which occurs during transportation can enhance the hydrolysis of the saturated ester in the drum.

The continuous process can be conducted by any suitable reaction methods, e.g., plug flow reactor or continuous stirred tank reactor, using the reaction conditions described above. The catalyst concentration in the continuous processes is selected to provide the desired residence time to achieve the desired extent of hydrolysis. Further details concerning the reaction conditions, apparatus and the like are known to those skilled in the art.

The invention is hereinafter described with respect to the Examples which are provided for illustrative purposes and are not intended to limit the scope of the claims which follow.

EXAMPLES

Table 1 below provides a cross reference for abbreviations and trade names used in the examples.

TABLE 1

| NAME | DESCRIPTION |
| --- | --- |
| MMA | methyl methacrylate |
| AA | acrylic acid |
| EA | ethyl acrylate |
| MAA | methacrylic acid |
| Aerosol ® OT-75 | an anionic diester sulfosuccinate surfactant having a surface tension of 32.2 dynes/cm and a molecular weight of 445 grams per gram mole and 75% active, available from American Cyanamid, Wayne, NJ. |
| Aerosol ® OT-100 | an anionic diester sulfosuccinate surfactant having a surface tension of 32.2 dynes/cm and a moleular weight of 445 grams per gram mole and 100% active, available from American Cyanamid, Wayne, NJ. |
| Amerhold ® DR-25 | A latex polymer made in accordance with the procedure described in Example 1 available from Amerchol Corporation, Edison, NJ |
| Triton ® X-100 | a nonionic ethoxylated alkyl phenol surfactant |

TABLE 1-continued

| NAME | DESCRIPTION |
|---|---|
| | having a surface tension of 30.0 dynes/cm and a molecular weight of 603 grams per gram mole, available from Union Carbide Corporation, Danbury, CT. |
| Triton ® X-200 | an anionic alkylaryl polyether sulfonate surfactant having a surface tension of 30.0 dynes/cm, available from Union Carbide Corporation, Danbury, CT. |
| Dymel ® A | dimethyl ether propellant, available from DuPont, Wilmington, DE. |
| Fluorad ® FC-430 | a nonionic fluorinated surfactant having a surface tension of 30.0 dynes/cm, available from 3M Company, St. Paul, MN. |
| nBM | n-butyl mercaptan |
| 2EHMP | 2-ethylhexyl-3-mercaptopropionate, available from Phillips 66 Company, Bartlesville, OK. |
| PS | volume average particle size, microns |
| Amphomer ® | a terpolymer of an octylacrylamide, butylaminoethyl methacrylate and an acrylate acid, available from National Starch and Chemical, Bridgewater, NJ. |
| Gantrez ® ES-225 | a copolymer of methyl vinyl ether and the ethyl half ester of maleic anhydride, available from International Specialty Products, Wayne, NJ. |
| SD Alcohol 40 | anhydrous ethanol, available from Pharmco Products Inc., Norwalk, CT. |
| Tergitol 15S9 | an ethoxylated linear secondary alcohol having a surface tension of 30.0 dynes/cm and a molecular weight of 584 grams per gram mole, available from Union Carbide Corporation, Danbury, CT. |
| Tergitol 15S40 | an ethoxylated linear secondary alcohol having a surface tension of 42.0 dynes/cm and a molecular weight of 2004 grams per gram mole, available from Union Carbide Corporation, Danbury, CT. |
| Aerosol NPES 930 | a nonyl phenol ether sulfate surfactant having a surface tension of 39.5 dynes/cm and a molecular weight of 713 grams per gram mole, available from Cytec Industries, Inc., West Paterson, NJ. |
| Aerosol NPES 2030 | a nonyl phenol ether sulfate surfactant having a surface tension of 44.0 dynes/cm and a molecular weight of 1200 grams per gram mole, available from Cytec Industries, Inc., West Paterson, NJ. |
| Aerosol NPES 3030 | a nonyl phenol ether sulfate surfactant having a surface tension of 48.2 dynes/cm and a molecular weight of 1640 grams per gram mole, available from Cytec Industries, Inc., West Paterson, NJ. |

Example 1

PREPARATION OF POLYMER COMPOSITION

A copolymer of MMA, EA and MAA was prepared as follows: Five hundred grams of MMA, EA, and MAA were weighed out in the weight ratio of 40/55/5. Half of one weight percent of nBM, based on the total monomer weight, and 0.5 weight percent Aerosol® OT-75 were added to the monomer mix. Then an initial charge of deionized water (1156 grams) and Aerosol® OT-75 (1.25 grams) were added to a 3 liter glass-jacketed reaction vessel equipped with a stirrer, condenser, and temperature control. The stirrer was set at 200 revolutions per minute (rpm) for the entire polymerization reaction, the vessel was purged with nitrogen, and the surfactant solution was heated to 80° C. A catalyst solution of 2.5 grams ammonium persulfate and 200 grams deionized water was quickly added to the heated reactor contents. About 5 minutes after adding the catalyst solution, the monomer mix was gradually added over a period of 150 minutes. At the end of the monomer feed, the aqueous dispersion product was maintained at 80° C. for 30 additional minutes. Post initiator solutions, 0.15 grams potassium persulfate in 25 grams water followed by 0.15 grams sodium metabisulfite in 25 grams water, were added and the dispersion was held at 80° C. for another 30 minutes and finally cooled to room temperature.

The resulting dispersion was filtered through a 200 mesh screen and left no scrap. It had a total solids of 26.3 weight percent, a volume average particle size of 0.2 microns, and a pH of 2.5. Its number average molecular weight (Mn) was 21,000 and its glass transition onset (Tg), after equilibrating the polymer at 0% relative humidity for three days, was 30° C.

Examples 2–19

PREPARATION OF POLYMER COMPOSITIONS

Copolymer samples using different surfactants were prepared using the following procedure (Surfactants and amounts are shown for Example 3). The terminology used to describe the surfactants in the following Examples is "primary" and "secondary." The primary surfactant was present in the Initial reactor charge and, in addition, fed during the course of the polymerization. Because Aerosol OT was soluble in the Monomer mix, the portion fed during the course of the polymerization was combined with the Monomer mix. The NPES and Tergitol 15S surfactants, on the other hand, were insoluble in Monomer mix; consequently, the portion fed during the course of the polymerization was combined with the Fed catalyst. In all runs, the secondary surfactant was present only in the Initial reactor charge.

| | | COMPONENT | GRAMS |
|---|---|---|---|
| (A) | Initial reactor charge | 1. deionized water | 1361.00 |
| | | 2. Primary Surfactant Aerosol OT (75%) | 1.49 |
| | | 3. Secondary Surfactant Triton X-100 | 8.21 |
| (B) | Initial Catalyst | 4. ammonium persulfate (+22.5 g water) | 2.25 |
| (C) | Fed monomer | 5. Monomer mix | 605.73 |
| (D) | Fed catalyst | 6. ammonium persulfate (+30 g water) | 0.75 |
| (E) | Post catalyst | 7. ammonium persulfate (0.25 g in 10.0 g water) | 0.25 |
| (F) | preservative | 8. hydrogen peroxide (30%) | 20.00 |
| (G) | Monomer mix | | |
| | | wt % | grams |
| | MMA | 34.0 | 204.00 |
| | EA | 56.0 | 336.00 |
| | AA | 5.0 | 30.00 |
| | MAA | 5.0 | 30.00 |
| | 2EHMP | | 2.73 |
| | Primary Surfactant Aerosol OT (75%) | | 3.00 |
| | | | 605.73 |

The Initial Reactor Charge was introduced to a 3 liter, glass-jacketed reaction vessel equipped with a stirrer. The stirrer was set at 300 rpm throughout run, the vessel was blanketed with nitrogen and heated to 80° C. The Initial Catalyst was pumped in over 2 minutes and the temperature was maintained at 80° C. 5 minutes after adding initial catalyst, the Fed Monomer was pumped in over 180 minutes. 90 minutes after the beginning of the monomer feed, the Fed Catalyst was pumped in over 105 minutes. The temperature was maintained at 80° C. for 60 minutes after the end of catalyst feed. Then the Post Catalyst was pumped in over 60 minutes. The temperature and stirring was maintained for 30 minutes after the end of post catalyst feed. The reaction product was then cooled to room temperature.

The reaction product was then visually inspected and the viscosity and particle size were measured. The viscosity measurement was performed as described above, and the particle size was measured using a light scattering technique. Further details of particle size measurement are known to those skilled in the art. The results of Examples 2–19 are shown in Table 2 below.

Example 20

Forty-three enzymes were screened for ethyl propionate hydrolysis in either ethyl acrylate or Amerchold® Dr-25. A description of the enzymes is listed in Table 4. After the screening, the best enzymes were used to pretreat the feed in biphasic mixtures or to posttreat the latex using continuous and batch reactors as further described hereinafter.

TABLE 2

| EXAMPLE | PRIMARY SURFACTANT | SECONDARY SURFACTANT | VISUAL INSPECTION | 1st freeze/thaw viscosity (cP) | 2nd freeze/thaw viscosity (cP) | 3rd freeze/thaw viscosity (cP) |
|---|---|---|---|---|---|---|
| 2 | Aerosol OT | None | slight gel | >5000 thick gel | >5000 thick gel | >5000 thick gel |
| 3 | Aerosol OT | Triton X-100 | slight gel | 1500 grainy gels | 1000 grainy gels | 260 grainy gels |
| 4 | Aerosol OT | NPES 930 | gel | 15 gel layer | 28 gel layer | 37 gel layer |
| 5 | Aerosol OT | NPES 2030 | gel | 32 gel layer | 17 gel layer | 19 gel layer |
| 6 | Aerosol OT | NPES 3030 | gel | 165 grainy, lumpy gels | 540 grainy, lumpy gels | 820 grainy, lumpy gels |
| 7 | Aerosol OT | Tergitol 15S9 | gel | 14 clean | 110 clean | 300 gel layer |
| 8 | Aerosol OT | Tergitol 15S40 | gel | 13 gel layer | 15 gel layer | 12 gel layer |
| 9 | NPES 930 | None | slight gel | 10 clean | 10 clean | 10 clean |
| 10 | NPES 930 | Triton X-100 | gel | 29 clean | 29 clean | 26 clean |
| 17 | NPES 930 | Tergitol 15S9 | gel | 12 gel layer | 14 gel layer | 15 gel layer |
| 12 | NPES 930 | Tergitol 15S40 | gel | 13 small gel layer | 13 small gel layer | 12 small gel layer |
| 13 | NPES 2030 | None | gel | 10 clean | 10 clean | 10 clean |
| 14 | NPES 2030 | Triton X-100 | slight gel | 350 floating gels | 900 floating gels | 900 floating gels |
| 15 | NPES 2030 | 15S9 | gel | 27 clean | 20 clean | 22 clean |
| 16 | NPES 2030 | 15S40 | gel | 12 gel layer | 13 gel layer | 11 gel layer |
| 17 | NPES 3030 | None | ½ inch gel | too unstable to test | too unstable to test | too unstable to test |
| 18 | Tergitol 15S40 | None | slight gel | 51 clean | 60 clean | 69 clean |
| 19 | Tergitol 15S9 | None | slight gel | >5000 thick gel | >5000 thick gel | >5000 thick gel |

Table 3, below, sets forth certain physical characteristics of the surfactants used in Examples 2–19.

TABLE 3

| Surfactant | Ionic Character | Surface Tension dynes/cm | Molecular Weight grams/gram mole |
|---|---|---|---|
| Aerosol OT | anionic | 32.2 | 445 |
| Triton X-100 | nonionic | 30.0 | 603 |
| Tergitol 15S9 | nonionic | 30.0 | 584 |
| Tergitol 15S40 | nonionic | 42.0 | 2004 |
| Aerosol NPES 930 | nonionic and anionic | 39.5 | 713 |
| Aerosol NPES 2733 | nonionic and anionic | 44.0 | 1200 |
| Aerosol NPES 3030 | nonionic and anionic | 48.2 | 1640 |

TABLE 4

ENZYMES SCREENED FOR THE HYDROLYSIS OF ETHYL PROPIONATE IN ETHYL ACRYLATE OR IN LATEX OF EXAMPLE 1

| ENZYME | TYPE | SOURCE or COMMON NAME | OTHER INFORMATION | COMPANY |
|---|---|---|---|---|
| L-1754 | Lipase | Candida rugosa | | Sigma |
| L-1150 | Lipase | Candida rugosa | Immobilized on acrylic beads | Sigma |
| L-3001 | Lipase | Wheat Germ | | Sigma |
| L-3126 | Lipase | Porcine Pancreas | | Sigma |
| P-5380 | Protease | Subtilisin Carlsberg | | Sigma |
| P-1512 | Protease | Thermolysin | | Sigma |
| P-4032 | Protease | Aspergillus oryzae | | Sigma |
| P-4630 | Protease | Bovine Pancreas | | Sigma |
| P-4755 | Protease | Aspergillus oryzae | | Sigma |
| P-0384 | Protease | Streptomyces caespitosus | | Sigma |
| P-6141 | Protease | Bacillus polymyxa | | Sigma |
| P-5147 | Protease | Streptomyces griseus | | Sigma |
| P-5027 | Protease | Rhizopus species | Newlase | Sigma |

TABLE 4-continued

ENZYMES SCREENED FOR THE HYDROLYSIS OF
ETHYL PROPIONATE IN ETHYL ACRYLATE OR
IN LATEX OF EXAMPLE 1

| ENZYME | TYPE | SOURCE or COMMON NAME | OTHER INFORMATION | COMPANY |
|---|---|---|---|---|
| P-7026 | Protease | Aspergillus sojae | | Sigma |
| P-3375 | Protease | Papain | | Sigma |
| P-7545 | Protease | Porcine Pancreas | Pancreatin | Sigma |
| C-4129 | Protease | Bovine Pancreas | Chymotrypsin | Sigma |
| 62305 | Lipase | Rhizopus arrhizus | | Fluka |
| ChiroCLEC CR | Lipase | Candida rugosa | Cross-linked enzyme crystals | Altus Biologics |
| CCL | Lipase | Candida rugosa | | Altus Biologics |
| CCE | Esterase | Candida rugosa | | Altus Biologics |
| D-L-1754 | Lipase | L-1754 (Candida rugosa) | Freeze dried with sucrose | Jon Dordick (U. Iowa) |
| Novozym 435 | Lipase | Candida antarctica | Immobilized on acrylic resin | Novo |
| Novozym 525 | Lipase | Candida antarctica | | Novo |
| Lipozyme 10000L | Lipase | Mucor miehei | Liquid | Novo |
| Lipozyme IM 60 | Lipase | Mucor miehei | | Novo |
| Lipolase 100 T | Lipase | Fungal origin | | Novo |
| Esperase 6.0 T | Protease | Bacillus species | | Novo |
| Neutrase 1.5 MG | Protease | Bacillus subtilis | | Novo |
| Alcalase 3.0 T | Protease | Bacillus licheniformis | | Novo |
| Savinase 6.0 T | Protease | Bacillus species | | Novo |
| Termamyl 60 T | Amylase | Bacillus licheniformis | | Novo |
| Lipase AK | Lipase | Pseudomonas species | | Amano |
| Lipase PS-30 | Lipase | Pseudomonas species | | Amano |
| Lipase AY-30 | Lipase | Candida rugosa | | Amano |
| AY-L | Lipase | Candida rugosa | Liquid | Amano |
| Proleather | Protease | Bacillus subtilis | | Amano |
| L-10 | Lipase | Candida lipolytica | | Amano |
| CE | Lipase | Humicola langinosa | | Amano |
| CES | Lipase | Pseudomonas species | | Amano |
| MAP-10 | Lipase | Mucor javanicus | | Amano |
| Protease N | Protease | Bacillus subtilis | | Amano |
| Prozyme 6 | Protease | Aspergillus oryzae | | Amano |

The company locations for the enzymes as listed in Table 4 are:

Fluka Chemical Corp., 980 South 2nd Street, Ronkonkoma, N.Y. 11779.

Sigma Chemical Company, P.O. Box 14508, St. Louis, Mo. 63178.

Amano International Enzyme Co., Inc. P.O. Box 1000, Troy, Va. 22974.

Altus Biologics Inc., 40 Allston Street, Cambridge, Mass. 02139.

Novo Nordisk Biochem North America, Inc., State Road 1003, Box 576, Franklinton, N.C. 27525.

The reaction mixtures were analyzed by gas chromatography (1 milliliter ("ml"), manual injection) using a Hewlett Packard 5890 equipped with a flame ionization detector on a 30 meter ("m") DB-WAX column. Toluene was used as an internal standard and acetone was used to solubilize the latex particles.

Example 20-A

In this Example, the feed comprised ethyl acrylate (90 wt %) and ethyl propionate (10 wt %). The procedure for catalyst screening was as follows. Four mls of fresh 9:1 (by weight) ethyl acrylate:ethyl propionate were added to 10 ml glass flasks with 400 mg enzyme. Then, the ethyl acrylate-:ethyl propionate mixture was presaturated with 10 vol % water in a sonic bath. The flasks were placed in a New Brunswick Innova 4000 Incubator Shaker (200 RPM, 30° C.).

Thirty-eight enzymes were screened using mixtures of 9:1 ethyl acrylate:ethyl propionate (by weight) saturated with $H_2O$ (~1 wt %). To compare activity, the production of propionic acid (from ethyl propionate hydrolysis) and acrylic acid (from ethyl acrylate hydrolysis) was measured. To compare selectivity for ethyl priopionate over ethyl acrylate hydrolysis, the relative yield of propionic versus acrylic acid was determined. Enzymes showing moderate to very good activity are listed in Table 5.

TABLE 5

ACTIVITY (MEASURED BY PROPIONIC AND ACRYLIC ACID PRODUCTION) AND
SELECTIVITY (MEASURED BY RELATIVE YIELD) FOR THE ENZYME CATALYZED
HYDROLYSIS OF ETHYL PROPIONATE IN ETHYL ACRYLATE

ENZYMES SHOWING MODERATE TO VERY GOOD ACTIVITY

| ENZYME | REACTION TIME (hrs) | PROPIONIC ACID (wt %) | ACRYLIC ACID (wt %) | RELATIVE YIELD (Propionic Acid/Acrylic Acid)* |
|---|---|---|---|---|
| None (Control) | 240 | 0.0 | 0.0 | — |
| L-1754 | 4 | 1.8 | 0.3 | 50.3 |

TABLE 5-continued

ACTIVITY (MEASURED BY PROPIONIC AND ACRYLIC ACID PRODUCTION) AND
SELECTIVITY (MEASURED BY RELATIVE YIELD) FOR THE ENZYME CATALYZED
HYDROLYSIS OF ETHYL PROPIONATE IN ETHYL ACRYLATE

ENZYMES SHOWING MODERATE TO VERY GOOD ACTIVITY

| ENZYME | REACTION TIME (hrs) | PROPIONIC ACID (wt %) | ACRYLIC ACID (wt %) | RELATIVE YIELD (Propionic Acid/Acrylic Acid)* |
|---|---|---|---|---|
| Lipozyme IM 60 | 5 | 1.8 | 0.2 | 88.9 |
| Lipase AY-30 | 5 | 1.2 | 0.4 | 31.8 |
| CCE | 6 | 1.2 | 0.2 | 31.8 |
| CE | 5 | 0.3 | 0.02 | 118.2 |
| MAP-10 | 4 | 0.3 | 0.0 | ● |
| 62305 | 6 | 0.1 | 0.0 | ● |
| L-3126 | 5 | 0.4 | 0.6 | 5.3 |
| Lipase AK | 4 | 0.3 | 0.8 | 3.5 |
| Lipase PS-30 | 5 | 1.0 | 4.2 | 2.2 |
| P-7545 | 7 | 0.2 | 0.3 | 6.0 |
| Novozym 435 | 2 | 1.2 | 4.2 | 2.7 |
| Protease N | 3 | 0.01 | 0.02 | 4.4 |
| D-L-1754 | 4 | 0.02 | 0.03 | 6.9 |
| CCL 5 | 1.2 | 1.6 | 6.4 | |
| Lipolase 100 T | 6 | 0.5 | 4.5 | 0.9 |

*RELATIVE YIELD = Propionic Acid Yield/Acrylic Acid Yield =
(Moles Propionic Acid Produced/Initial Moles Ethyl Propionate)
(Moles Acrylic Acid Produced/Initial Moles Ethyl Acrylate)
Reaction Conditions: 100 mg/ml enzyme, 9:1 Ethyl Acrylate:Ethyl Propionate by weight, Saturated with water (~1 wt %), 30° C. Shaking speed 200 RPM (Incubator-shaker)

L-1754, Lipozyme, AY-30, and CCE showed the best combination of activity and selectivity. They were 32–89 times more selective for ethyl propionate and hydrolyzed 20–30% of ethyl propionate in 6 hours ("hrs"). Enzymes CE, MAP-10, and 62305 were the most selective catalysts, and Novozym 435, PS-30, and Lipolase were the most active. Lipolase was the only enzyme of 38 tested that selectively hydrolyzed ethyl acrylate over ethyl propionate. Enzymes showing very low to no activity are listed in Table 6. Preferably, the enzymes used in accordance with the present invention are effective to provide a relative yield (as defined in Table 5) of greater than 1, preferably greater than 2 and more preferably greater than 4.

TABLE 6

ENZYMES SHOWING VERY LOW TO NO ACTIVITY
(MEASURED BY PROPIONIC AND ACRYLIC ACID
PRODUCTION) FOR THE ENZYME CATALYZED
HYDROLYSIS OF ETHYL PROPIONATE IN ETHYL
ACRYLATE

| ENZYME | TIME (hrs) | PROPONIC ACID (wt %) | ACRYLIC ACID (wt %) |
|---|---|---|---|
| P-4032 | 192 | 0.3 | 0.05 |
| P-5380 | 96 | 0.1 | 0.04 |
| Savinase 6.0 T | 144 | 0.1 | 0 |
| P-3375 | 26 | 0.03 | 0.0 |
| CES | 48 | 0.2 | 0.8 |
| Prozyme 6 | 24 | 0.03 | 0.0 |
| L-3001 | 25 | 0.0 | 0.0 |
| P-1512 | 96 | 0.0 | 0.0 |
| Proleather | 144 | 0.0 | 0.0 |
| P-5147 | 25 | 0.0 | 0.0 |
| C-4129 | 26 | 0.0 | 0.0 |
| Neutrase 1.5 MG | 25 | 0.0 | 0.0 |
| Alcalase 3.0 T | 26 | 0.0 | 0.0 |
| Esperase 6.0 T | 27 | 0.0 | 0.0 |
| L-10 | 26 | 0.0 | 0.0 |
| P-4630 | 20 | 0.0 | 0.0 |
| P-4755 | 21 | 0.0 | 0.0 |
| P-0384 | 22 | 0.0 | 0.0 |
| P-6141 | 21 | 0.0 | 0.0 |
| P-5027 | 22 | 0.0 | 0.0 |
| P-7026 | 23 | 0.0 | 0.0 |
| Termamyl 60 T | 24 | 0.0 | 0.0 |

Reaction Conditions: 100 mg/ml enzyme, 9:1 Ethyl Acrylate: Ethyl Propionate by weight, saturated with water (~1 wt %), 30° C., Shaking speed 200 RPM (Incubator-shaker)

Example 20-B

In this Example, to increase ethyl propionate hydrolysis and overcome equilibrium constraints imposed by water-saturated ethyl acrylate (only 1 wt % water), the best (combination of selectivity and activity) immobilized enzyme, Lipozyme, was used in two-phase aqueous-organic mixtures. Non-immobilized enzymes were also used but partitioned into the water phase. For two-phase mixtures, 10, 50, or 90 vol % water was added directly to reaction flasks containing either 9:1 or 99:1 ethyl acrylate:ethyl propionate, and these flasks were then placed in an incubator-shaker as in Example 20-A. For larger scale experiments using biphasic solutions, either 35 or 7 mls of 99:1 ethyl acrylate:ethyl propionate were added to a 200 ml round-bottom flask with either 3500 or 700 mg enzyme (100 mg/ml on water-free basis). Then either 35 or 63 mls water (for 50 and 90 vol % water solutions) were added. A side-arm, overhead impeller at 250 RPM was used to provide mixing and the temperature was controlled (30° C.) with a heating mantle.

At first, the overall hydrolysis of ethyl propionate was increased by adding 50 vol % water, but the rate of hydrolysis actually decreased. These were mixed in an incubator-shaker, where poor mixing between the phases and between Lipozyme and reactants slowed ethyl propionate hydrolysis. In fact, Lipozyme pooled in the bottom water layer. Still, the 50% water system provided a constant supply of water, continually driving ethyl propionate hydrolysis.

To improve mixing, an overhead impeller in a larger reactor was used. This significantly increased ethyl propionate hydrolysis in a 99:1 ethyl acrylate:ethyl propionate feed. Using a 50:50 aqueous:organic mixture in the shaker, the ethyl propionate concentration decreased 49% in 23 hrs while with the impeller, it decreased 80% in 26 hrs. The ethyl propionate hydrolysis was increased further by raising the water content to 90 vol %, decreasing the ethyl propionate concentration 97% in 23 hrs. Importantly, the ethyl acrylate concentration remained fairly constant, decreasing only 0.16% in 23 hrs with the 90:10 aqueous-organic mixture (and 99:1 ethyl acrylate:ethyl propionate feed).

Example 20-C

In this Example the Amerhold DR25 was treated with enzymes. The procedure for screening was as follows. The appropriate amount of enzyme was added to 20 mls of Amerhold DR-25 and the reaction flasks were placed in the incubator-shaker (200 RPM, 30° C.). For larger scale reactions, the enzyme was added to 400 mls or more of the latex and an overhead stirrer (300 RPM) and heating mantle (typically 30° C.) were used.

For continuous reactor studies, the latex Amerhold DR-25 was fed into the top of a tubular reactor packed with glass beads (preheater) and 1 gram ("g") Novozym 435. The flowrate was controlled using a Gilson Model 302 pump and the reactor temperature was controlled using an outer jacket (tube). A mixture of propylene glycol and water was fed to the jacket from a temperature-controlled circulating bath. For sampling, 2.5 mls fresh sample was collected directly from the reactor outlet rather than from the product collector.

In this Example, 15 enzymes were screened (eleven of the best from the previous screening and four additional) to find the most active for ethyl propionate hydrolysis in Amerhold DR-25. Ethyl acrylate was also hydrolyzed although more slowly, and the disappearance of ethyl propionate and ethyl acrylate was measured to evaluate activity (Table 7). Novozym 435 was the most active and was used in further studies in batch reactors and in a continuous tube.

TABLE 7

CONCENTRATIONS OF ETHYL PROPIONATE AND ETHYL ACRYLATE IN THE ENZYME CATALYZED HYDROLYSIS OF ETHYL PROPIONATE AND ETHYL ACRYLATE IN AMERHOLD DR-25

| ENZYME | ENZYME CONC (wt %) | TIME (hrs) | ETHYL PROPIONATE (ppm) | ETHYL ACRYLATE (ppm) |
|---|---|---|---|---|
| None (Control) | — | 0 | 91 | 139 |
|  |  | 24 | 93 | 140 |
| Novozym 435 | 0.09 | 0 | 117 | 200 |
|  |  | 4 | 0 | 121 |
| Lipozyme IM 60 | 0.9 | 0 | 91 | 139 |
|  |  | 4 | 27 | 132 |
| PS-30 | 0.9 | 0 | 114 | 196 |
|  |  | 4 | 34 | 141 |
| ChiroCLEC CR | 0.09 | 0 | 109 | 171 |
|  |  | 4 | 28 | 146 |
| L-1754 | 0.9 | 0 | 91 | 139 |
|  |  | 24 | 33 | 125 |

TABLE 7-continued

CONCENTRATIONS OF ETHYL PROPIONATE AND ETHYL ACRYLATE IN THE ENZYME CATALYZED HYDROLYSIS OF ETHYL PROPIONATE AND ETHYL ACRYLATE IN AMERHOLD DR-25

| ENZYME | ENZYME CONC (wt %) | TIME (hrs) | ETHYL PROPIONATE (ppm) | ETHYL ACRYLATE (ppm) |
|---|---|---|---|---|
| 62305 | 0.9 | 0 | 97 | 145 |
|  |  | 24 | 30 | 156 |
| AY-30 | 0.9 | 0 | 112 | 112 |
|  |  | 24 | 27 | 159 |
| Lipolase 100 T | 0.9 | 0 | 114 | 196 |
|  |  | 24 | 25 | 141 |
| L-3126 | 0.9 | 0 | 92 | 178 |
|  |  | 24 | 9 | 97 |
| Lypozyme 10000 L | 0.9 | 0 | 92 | 178 |
|  |  | 24 | 15 | 155 |
| CE | 0.9 | 0 | 97 | 149 |
|  |  | 24 | 62 | 129 |
| MAP-10 | 0.9 | 0 | 97 | 149 |
|  |  | 24 | 79 | 151 |
| CCE | 0.9 | 0 | 112 | 112 |
|  |  | 24 | 76 | 181 |
| L-1150 | 0.9 | 0 | 114 | 196 |
|  |  | 24 | 94 | 186 |
| AY-L | 0.9 | 0 | 92 | 178 |
|  |  | 24 | 53 | 172 |

Reaction Conditions: 30° C., Shaking speed 200 RPM (Incubator-shaker)

Example 20-D

In this Example, ethyl propionate was hydrolyzed from Amerhold DR-25 using 1 g Novozym 435 in a continuous, packed-bed tubular reactor. Residual ethyl acrylate was also hydrolyzed, but to a smaller extent. Three runs with fresh catalyst were made. In the first, Novozym 435 maintained activity at 30° C. for 653 hrs, but quickly deactivated at 50° C. In the second run using fresh catalyst at 60° C. and 50 mls/hr latex flowrate, higher initial activity but quick deactivation was seen. In the last run also at 30° C., deactivation accrued throughout the run, but still good activity was seen. It is not known why the catalyst slowly deactivated in this run but not in the first, although the inlet ethyl propionate concentration was higher in this last run.

Example 20-E

In this Example, Novozym 435 was used to hydrolyze ethyl propionate from Amerhold DR-25 in a batch reactor at three different concentrations, 10000, 1000, and 100 ppmw Novozym 435. Using 10000 ppmw Novozym 435, the ethyl propionate was completely hydrolyzed from 112 ppmw to 0 ppmw (undetected by GC) in less than one hour, while the residual ethyl acrylate in the latex was reduced from 112 ppmw to 62 ppmw in one hour and to 8 ppmw in 24 hrs. Using 1000 and 100 ppmw enzyme, the ethyl propionate was completely hydrolyzed in less than 4 and 12 hours respectively. Residual ethyl acrylate was again also reduced, but much less than ethyl propionate.

This Example demonstrates that all of the ethyl propionate could be removed within 1 hr. However, because of high catalyst cost, the lowest enzyme concentration, 100 ppmw (0.01 wt %), may be more preferred for commercial use.

In general, posttreating the latex is generally preferred over pretreating the feedstock. Hydrolysis in water-based latex requires less enzyme, less reaction time, no liquid separation of phases, and produces no added waste.

Similarly, a batch process may often be preferred to treat the latex over a continuous process, as the continuous process requires significant capital investment while the batch process can often be easily retrofitted into existing facilities having appropriate temperature and agitation control.

In addition, although recycling immobilized enzymes, e.g., Novozym 435, may reduce catalyst cost significantly, it can be difficult and labor intensive in small-scale batch facilities. Thus, it is also possible to use more concentrated, non-immobilized enzymes, e.g., Novozym 525, at ten fold or lower concentrations. Such non-immobilized enzymes can be used in existing batch facilities (as with the immobilized enzymes), or alternatively they can be added to the latex to let them hydrolyze the saturated esters during shipment rather than using valuable reactor time in plant facilities.

Although the invention has been described with respect to specific aspects, those skilled in the art will recognize that other aspects are intended to be included in the scope of the claims which follow.

We claim:

1. A process for selectively hydrolyzing a saturated ester over an unsaturated ester, said saturated and unsaturated ester each comprising from 1 to about 5 carbon atoms in the alkyl group, said process comprising contacting a feed containing said unsaturated ester and said saturated ester at a pH of from about 4 to 8 and a temperature of from about 20° to 50° C. with an enzyme having (i) functionality to hydrolyze esters and (ii) selectivity for said saturated ester over said unsaturated ester to convert said saturated ester to its corresponding acid and alcohol.

2. The process of claim 1 wherein the saturated ester is ethyl propionate.

3. The process of claim 1 wherein the unsaturated ester is ethyl acrylate.

4. The process of claim 1 wherein the enzyme is a lipase.

5. The process of claim 4 wherein the enzyme is a *Candida antarctica* lipase enzyme.

6. The process of claim 1 wherein the enzyme is an esterase.

7. The process of claim 1 wherein the feed comprises from about 10 ppmw to 10 wt % of said saturated ester.

8. The process of claim 7 wherein the feed comprises from about 70 to 99 wt % of said unsaturated ester.

9. The process of claim 8 wherein the feed comprises less than about 10 wt % water.

10. The process of claim 7 wherein the feed further comprises from about 10 to 60 wt % of a latex polymer polymerized from said unsaturated ester, and optionally other monomers.

11. The process of claim 10 wherein the feed comprises from about 40 to 90 wt % water.

12. A process for selectively hydrolyzing a saturated ester over an unsaturated ester, said saturated and unsaturated ester each comprising from 1 to about 5 carbon atoms in the alkyl group, said process comprising contacting a feed containing said unsaturated ester, said saturated ester, water and a latex polymer polymerized from said unsaturated ester and optionally other monomers at a pH of from about 4 to 8 and a temperature of from about 20° to 50° C. with an enzyme having (i) functionality to hydrolyze esters and (ii) selectivity for said saturated ester over said unsaturated ester to convert said saturated ester to its corresponding acid and alcohol.

13. The process of claim 12 wherein the saturated ester is ethyl propionate.

14. The process of claim 12 wherein the unsaturated ester is ethyl acrylate.

15. The process of claim 12 wherein the enzyme is a *Candida antarctica* lipase enzyme.

16. The process of claim 12 wherein said enzyme is added to the feed and the feed is separated into a plurality of portions prior to any significant hydrolysis of said saturated ester.

17. The process of claim 16 wherein each portion of the feed is introduced into a separate container prior to any significant hydrolysis of the saturated ester.

18. The process of claim 17 wherein the concentration of the enzyme in said container is from about 0.1 to 100 ppmw based on the total weight of the feed.

19. The process of claim 18 further comprising agitating said container to promote the hydrolysis of said saturated ester.

20. A process for selectively hydrolyzing ethyl propionate over ethyl acrylate comprising contacting a feed containing said ethyl propionate and said ethyl acrylate at a pH of from about 5 to 7 and a temperature of from about 25° to 40° C. with a *Candida artarctica* lipase enzyme having (i) functionality to hydrolyze esters and (ii) selectivity for said ethyl propionate over said ethyl acrylate to convert said ethyl propionate to propionic acid and ethyl alcohol.

* * * * *